(12) United States Patent
Rubin et al.

(10) Patent No.: US 7,972,775 B2
(45) Date of Patent: Jul. 5, 2011

(54) METHOD OF RISK MANAGEMENT FOR PATIENTS UNDERGOING NATALIZUMAB TREATMENT

(75) Inventors: Keith H. Rubin, Fort Lauderdale, FL (US); Steven Glazer, Weston, CT (US)

(73) Assignee: Seedlings Life Science Ventures, LLC, New York, NY (US)

( * ) Notice: Subject to any disclaimer, the term of this patent is extended or adjusted under 35 U.S.C. 154(b) by 492 days.

(21) Appl. No.: 11/885,615

(22) PCT Filed: Feb. 24, 2006

(86) PCT No.: PCT/US2006/006723
§ 371 (c)(1),
(2), (4) Date: Mar. 25, 2008

(87) PCT Pub. No.: WO2006/112951
PCT Pub. Date: Oct. 26, 2006

(65) Prior Publication Data
US 2009/0216107 A1  Aug. 27, 2009

Related U.S. Application Data

(60) Provisional application No. 60/658,335, filed on Mar. 3, 2005.

(51) Int. Cl.
*C12Q 1/70* (2006.01)
(52) U.S. Cl. .......................................... 435/5; 536/24.32
(58) Field of Classification Search .................. None
See application file for complete search history.

(56) References Cited

U.S. PATENT DOCUMENTS

2005/0095246 A1  5/2005 Shafer

OTHER PUBLICATIONS

Colucci et al (Journal of the Neurological Sciences, 2004. vol. 217, pp. 107-110).*
Sepkowitz (CID, 2002, vol. 34, pp. 1098-1107).*
FDA approved package insert for Tysabri as of Mar. 2005, 11 pgs.
Hammarin, et al., "Analysis of PCR as a Tool for Detection of JC Virus DNA in Cerebrospinal Fluid for Diagnosis of Progressive Multifocal Leukoencephalopathy", *Journal of Clinical Microbiology*, 34(12):2929-2932, Dec. 1996.
McGuire, et al., "JC Virus DNA in Cerebrospinal Fluid of Human Immunodeficiency Virus-infected Patients: Predictive Value for Progressive Multifocal Leukoencephalopathy", *Annals. of Neurology*, 37(3):395-399, Mar. 1995.
De Luca, et al., "Improved Detection of JC Virus DNA in Cerebrospinal Fluid for Diagnosis of AIDS-Related Progressive Multifocal Leukoencephalopathy," *Journal of Clinical Microbiology*, 34(5):1343-1346, May 1996.
"JC Virus DNA PCR for Diagnosis of PML", *Clinical Virology Laboratory Newsletter*, from the Department of Laboratory Medicine—Yale-New Haven Hospital Medical Center, 14(1), Jan. 2005, 2 pgs.
De Viedma, et al., "Dual Qualitative-Quantitative Nested PCR for Detection of JC Virus in Cerebrospinal Fluid: High Potential for Evaluation and Monitoring of Progressive Multifocal Leukoencephalopathy in AIS Patients Receiving Highly Active Antiretroviral Therapy", *Journal of Clinical Microbiology*, 37(3):724-728, Mar. 1999.
Koralnik, et al., "JC Virus DNS load in Patients With and Without Progressive Multifocal Leukoencephalopathy", *Neurology*, vol. 52, Issue 2, Jan. 1999, 14 pgs.
Ryschkewitsch, et al. "Comparison of PCR-Southern Hybridization and Quantitative Real-Time PCR for the Detection of JC and BK Viral Nucleotide Sequences in Urine and Cerebrospinal Fluid", *Journal of Virological Methods* 121(2):217-221, 2004.
Vago, et al., "JCV-DNA and BKV-DNA in the CNS Tissue and CSF of AIDS Patients and Normal Subjects. Study of 41 Cases and Review of the Literature", *Journal of Acquired Immune Deficiency Syndromes and Human Retrovirology*, 12:139-146, 1996.
Safdar, et al., "Fatal Immune Restoration Disease in Human Immunodeficiency Virus Type 1-Infected Patients with Progressive Multifocal Leukoencephalopathy: Impact of Antiretroviral Therapy-Associated Immune Reconstitution", Clinical Infectious Diseases, 35:1250-7, Nov. 15, 2002.
Ferrante, et al., "Detection of JC Virus DNA in Cerebrospinal Fluid from Multiple Sclerosis Patients", *Multiple Sclerosis*, 4:49-54, 1998.
Giudici, et al., "Highly Active Antiretroviral Therapy and Progressive Multifocal Leukoencephalopathy: Effects on Cerebrospinal Fluid Markers of JC Virus Replication and Immune Response", *Clinical Infectious Diseases*, 30:95-99, 2000.
Bowers, "Progressive Multifocal Leukoencephalopathy", *Bulletin of Experimental Treatments for AIDS*, by the San Francisco AIDS Foundation, Sep. 1997, 12 pgs.
Frohman, et al., "The Utility of MRI in Suspected MS—Report of the Therapeutics and Technology Assessment Subcommittee of the American Academy of Neurology", Neurology, 61:602-611, 2003.
Kappos, et al., "Natalizumab Treatment for Multiple Sclerosis: Recommendations for Patient Selection and Monitoring", *Lancet Neurology*, 6:431-441, May 2007.
Yousry, et al., "Evaluation of Patients Treated with Natalizumab for Progressive Multifocal Leukoencephalopathy", *The New England Journal of Medicine*, 354(9):924-933, 2006.
Rudick, et al., "Natalizumab Plus Interferon Beta-1a for Relapsing Multiple Sclerosis", *The New England Journal of Medicine*, 354(9):911-923, 2006.

(Continued)

*Primary Examiner* — Celine Qian
(74) *Attorney, Agent, or Firm* — Arthur Z. Bookstein

(57) ABSTRACT

Progressive multifocal leukoencephalopathy (PML) has been identified in patients taking natalizumab (NMAB) for the treatment of multiple sclerosis (MS). This patent application provides a novel method of patient screening and monitoring intended to decrease the risk of PML and other opportunistic central nervous system (CNS) diseases in patients undergoing MS therapy with NMAB, and proposes a novel method of screening and monitoring intended to decrease the risk of opportunistic disease processes of the CNS during the treatment of other medical disorders with NMAB.

14 Claims, No Drawings

OTHER PUBLICATIONS

Polman, et al., "A Randomized, Placebo-Controlled Trial of Natalizumab for Relapsing Multiple Sclerosis", *The New England Journal of Medicine*, 354(9):899-910.

Biogen/Elan website. Touch program to monitor patients using Tysabri (as required by the FDA when Tysabri returned to market): http://tysabri.com/tysbProject/tysb.portal/_baseurl/twoColLayout/SCSRepository/en_US/tysb/home/touch/index.html.

"Public Health Advisory—Suspended Marketing of Tysabri (Natalizumab)," Feb. 28, 2005, retrieved from the Internet Oct. 2, 2009: URL:http://www.fda.gov/Drugs/DrugSafety/PublicHealthAdvisories/ucm051761.htm, 3 pp.

Hans et al., "Progressive Multifocal Leukoencephalopathy after Natalizumab Monotherapy," *New England Journal of Medicine*, vol. 361, No. 11, Sep. 10, 2009, pp. 1081-1087.

Iacobaeus et al., "Analysis of Cerebrospinal Fluid and Cerebrospinal Fluid Cells From Patients With Multiple Sclerosis for Detection of JC Virus DNA," *Multiple Sclerosis* vol. 15, No. 1, Jan. 1, 2009, pp. 28-35.

Langer-Gould et al., "Progressive Multifocal Leukoencephalopathy in a Patient Treated With Natalizumab," *New England Journal of Medicine*, vol. 353, No. 4, Jul. 28, 2005, pp. 375-381.

Lima et al., "New Features of Progressive Multifocal Leukoencephalopathy in the Era of Highly Active Antiretroviral Therapy and Natalizumab," *Journal of Neurovirology*, vol. 11, No. Suppl. 3, 2005, pp. 52-77.

Noseworthy et al., "Natalizumab," *Nature Reviews*, vol. 4, No. 2, Feb. 1, 2005, retrieved from the Internet Oct. 2, 2009: URL:http://www.nature.com/nrd/journal/v4/n2/full/nrd1637.html, 6 pp.

Van Assche et al., "Progressive Multifocal Leukoencephalopathy After Natalizumab Therapy for Crohn's Disease," *The New England Journal of Medicine*, Jul. 28, 2005, vol. 353, No. 4, pp. 362-368.

Supplementary European Search Report for EP Application No. EP 06 76 970, completed Dec. 3, 2009, 3 pgs.

Dalton et al., "Effect of natalizumab on conversion of gadolinium enhancing lesions to T1 hypointense lesions in relapsing multiple sclerosis," *Journal of Neurovirology*, 2004, vol. 251, pp. 407-413.

Doggrell, S.A., "Is natalizumab a breakthrough in the treatment of multiple sclerosis?" *Expert Opinions in Pharmacotherapy*, 2003, vol. 4, No. 6, pp. 999-1001.

Du Pasquier et al., "A prospective study demonstrates an association between JC virus-specific cytotoxic T lymphocytes and early control of progressive multifocal leukoencephalopathy," *Brain*, 2004, vol. 127, pp. 1970-1978.

Sheridan, C., "Fast track to MS drug," *Nature Biotechnology*, Aug. 2004, vol. 22, No. 8, pp. 939-941.

Steiner, PML: underdiagnosed in MS patients on natalizumab, The Lancet Neurology, vol. 9, Issue 6, p. 564, Jun. 2010.

Sadiq, JCV detection in multiple sclerosis patients treated with natalizumab, J Neurology, Jan. 7, 2010.

Iacobeous, Analysis of cerebrospinal fluid and cerebrospinal cells from patients with multiple sclerosis for detection of JC virus DNA, Multiple Sclerosis 2009; 15:28-35.

Linda, Progressive Multifocal Leukoencephalopathy After Natalizumab Monotherapy, N Engl J Med 2009; 361:1081-7.

Communication dated Apr. 8, 2011 from European Patent Office in corresponding EPO Application 06 769 770.6-2406 (received Apr. 18, 2011).

* cited by examiner

METHOD OF RISK MANAGEMENT FOR PATIENTS UNDERGOING NATALIZUMAB TREATMENT

CROSS REFERENCE TO RELATED APPLICATIONS

This application is the national stage application of International Application No. PCT/US2006/006723, filed Feb. 24, 2006, which claims priority to and the benefit of U.S. Provisional Patent Application Ser. No. 60/658,225, filed Mar. 3, 2005.

BACKGROUND OF THE INVENTION

Natalizumab (NMAB) is a humanized antibody that binds to surface-expressed integrins on all leukocytes except neutrophils, and inhibits adhesion molecules on these leukocytes from binding to their counter-receptors. In so doing, NMAB disrupts the transmigration of these leukocytes across endothelial tissue and into inflamed parenchymal tissue. NMAB additionally inhibits recruitment and inflammatory activity of activated immune cells. Although the exact mechanism of action of NMAB is unclear, it is thought that at least part of the therapeutic benefit of NMAB in the treatment of MS is due to NMAB's ability to decrease the number of activated inflammatory cells, including T-lymphocytes, across the blood-brain barrier (BBB), thus decreasing the degree of inflammation within the CNS.

MS is considered to be a chronic inflammatory disease of the CNS, which is often due to myelin sheath and axonal CNS damage secondary to an autoimmune inflammatory process that usually includes a T-cell response. A more virus or toxin related demyelination has also been identified as a primary disorder within oligodendrocytes. In double blind, multi-center, placebo controlled trials, a therapeutic benefit of NMAB has been observed in patients with MS; and this is, at least in part, attributed to decreasing the extent of T-lymphocyte entry across the BBB and into the CNS, and therefore decreasing pathologic inflammatory disease within the CNS.

Unfortunately, in 2005 it was observed that three patients who had been treated with NMAB were diagnosed with Progressive Multi-focal Leukoencephalopathy (PML), a rare and often fatal disease of the brain that has been observed historically in immunosuppressed patients. While it is not definitively clear at the time of this application whether or not the diagnosed PML was caused by treatment with NMAB or simply associated with same, the inventors' understanding of the etiology of PML leads them to believe that the former is more likely. PML is progressive (over time it continues to encroach more and more brain tissue), multi-focal (occurs in more than one location within the brain), and is a disease of the white matter of the brain (leukoencephalopathy). Like MS, PML causes demyelination and can result in severe and often fatal neurological injury. The etiology of PML is understood to originate from a virus, the JC Virus, which can infect and kill oligodendrocytes, which are specialized neural cells that produce the myelin essential for proper neuronal function.

While still rare, the resurgence of PML during the past two decades was in part due to the compromised T-cell mediated immunity associated with patients with AIDS. In short, treatment with NMAB results in a CNS immunosuppression of sorts, akin (at least form the point of view of the CNS) to the more ubiquitous T-cell immunosuppression observed in patients with AIDS. It has also been observed that there is an association between JC Virus-specific cytotoxic T lymphocytes (CTL) and the early control of PML. That is, the more JC Virus-specific CTL, the more favorable outcome in patients with PML.

Although far from universal, prolonged PML survival after Highly Active Antiretroviral Therapy (HAART) (against the AIDS virus) has been reported and prolonged survival has been observed with JC Viral clearance from the CSF.

DESCRIPTION OF THE INVENTION

The invention relates in part to an appreciation that should PML or another opportunistic CNS disease occur as a result of CNS immunosuppression secondary to NMAB therapy, then the sooner NMAB therapy is discontinued, the more likely a patient will minimize CNS damage due to a CNS opportunistic disease, and the more likely that that same patient will recover. Because MS can be such a devastating disease, because treatment options for MS (and other medical disorders that may potentially benefit from NMAB therapy) are relatively limited, because NMAB has shown significant clinical benefit to MS patients in proper clinical studies, and because all medications carry risk and are assessed by their risk to benefit ratio, it may not be necessary to permanently remove NMAB as a therapeutic option for patients. Rather, it may be possible to create a means of managing the risk associated with NMAB, and in particular to produce a method of screening and monitoring patients undergoing NMAB therapy to minimize the risk of opportunistic CNS disease that may occur secondary to CNS immunosuppression.

The invention provides methods to address not only the risk of PML in patients treated with NMAB, but to also address other opportunistic diseases of the CNS that may result from a compromised CNS T-cell immune response due to treatment with NMAB. Diseases of the CNS that may occur as a result of CNS T-cell mediated immunosuppression include but are not limited to PML (secondary to the JC Virus), cytomegalovirus (CMV) infection, *toxoplasmosis, cryptococcosis, tuberculosis* (TB) and primary CNS lymphoma (PCL) which is almost always due to Epstein-Barr Virus (EBV).

PREFERRED MODES OF PRACTICING THE INVENTION

Prior To Beginning Treatment With NMAB A Baseline Screening Evaluation Should Be Undertaken Prior to beginning treatment with NMAB and prior to CSF assessment, a patient should first be required to have an MRI brain imaging study, which will also serve as a baseline study with which to compare future MRI brain images.

Prior to the initiation of NMAB therapy, cerebrospinal fluid (CSF) from the intended patient should be tested by polymerase chain reaction (PCR) (or other diagnostic assay if it is more sensitive) to detect the presence of one or more of CMV, JC Virus, *Toxoplasma gondii*, EBV, *Cryptococcus neoformans*, and TB.

Prior to beginning treatment with NMAB, a patient should also be required to have an ophthalmologic examination to establish and document a baseline retinal status and to rule out the presence of ocular CMV (the optic nerve is a component of the CNS and may be observed in part by a simple ocular examination).

The presence of a positive CSF PCR (or other more specific diagnostic test) for CMV, EBV, TB, JC Virus, *Toxoplasma gondii*, or *Cryptococcus neoformans*; or a diagnosis of CMV retinitis on ophthalmologic examination, should immediately disqualify a patient from treatment with NMAB.

Interval Monitoring In A Patient Undergoing Treatment With NMAB

Because it is not clear whether PML is due to an infection with a latent JC Virus, or a JC Virus acquired by exposure after CNS immunosuppression due to NMAB or AIDS, and because likewise is the case for CMV, TB, EBV, *Toxoplasma Gondii*, and *Cryptococcus neoformans*; it will be desirable to perform interval evaluations (and if necessary, interventions) of patients undergoing treatment with NMAB to reduce the risk of opportunistic disease resulting from CNS immunosuppression.

Interval Monitoring for patients undergoing NMAB treatment can be divided into two categories:
1) No Clinical Disease Progression: In this instance, a patient's history and physical exam demonstrate no progression of a patient's MS or other medical disorder, and no signs or symptoms of a potential opportunistic infection. As such, the Baseline Screening Evaluation should be performed on an annual basis and the patient's MS or other medical disorder should be treated according to standard treatment guidelines for the particular medical disorder. In this case, Interval Monitoring takes place on a regular annual basis.
2) Clinical Disease Progression: In this instance, when a patient's history and/or physical exam indicate a progression of the underlying medical disorder such as MS, or symptoms and/or signs of a potential opportunistic disease process; an additional screening process (the Progression Screening Process) is undertaken immediately upon identifying the progression to rule out a CNS opportunistic disease process. This screening process incorporates the same group of studies indicated for the Baseline Screening Evaluation. Again, it is important to perform the MRI brain imaging studies prior to performing CSF studies as toxoplasmosis can create a mass effect that might make a lumbar puncture contraindicated. While the inventors are not aware of an identified case of toxoplasmosis in a patient undergoing NMAB treatment, toxoplasmosis is a well-known and treatable opportunistic infection of the CNS in immunocompromised patients. Should greater numbers of patients undertake NMAB therapy, this opportunistic infection may arise. Thus, this precaution of prioritizing brain MRI evaluation before CSF examination is reasonable.

If MRI, CSF, or ophthalmologic examination of the Progression Screening Process uncovers an opportunistic CNS disease process, then NMAB therapy should be immediately discontinued and proper assessment and treatment of the identified opportunistic disease process should be undertaken.

If MRI, CSF, and ophthalmologic examination of the Progression Screening Process uncover no opportunistic disease, then a patient may continue NMAB therapy. In this case, within two weeks of the Progression Screening Process, a second lumbar puncture is performed to evaluate the CSF a second time (the Post-Progression Second Screen). Once again, the CSF is tested by PCR (or by another more sensitive assay if it is available) for one or more of CMV, JC Virus, EBV, TB, Toxoplasmosis, and Cryptococcus. The reason for the Post-Progression Second (CSF) Screen within two weeks of the Progression (CSF) Screen is the result of the imperfect sensitivity of PCR analysis. As examples, one diagnostic CSF PCR study for the JC Virus was 76% sensitive; another was 92% sensitive. Once a diagnostic study has a sensitivity of 99%, that particular CSF study can be eliminated from the Post-Progression Second (CSF) Screen.

If both the Progression Screening Process and the Post-Progression Second Screen provide no indication of an opportunistic disease process within the CNS, then the ongoing treatment of the patient with MS (or other medical disorder) continues according to standard treatment guidelines for the particular medical disorder.

Subsequently, if a patient's history and physical exam then indicate no progression of the underlying medical disorder such as MS, nor symptoms nor signs of a potential opportunistic disease process, then a Baseline Screening Evaluation should be repeated one year after the last negative Post-Progression Second Screen.

However, if subsequently a patient's history and/or physical exam indicate a positive progression of the underlying medical disorder such as MS, and/or signs or symptoms of a potential opportunistic CNS disease process, then the time for the next Progression Screening Process should be at a minimum of two to three months following the last negative Post-Progression Second Screen.

This Interval Monitoring continues for as long as a patient is treated with NMAB.

To emphasize, the proposed method of screening and monitoring patients undergoing NMAB treatment for MS and other medical disorders, is intended to minimize, but will not eliminate, the risk of opportunistic CNS disease that may occur as a result of impaired CNS T-cell immunity due to NMAB therapy.

We claim:

1. A method of reducing the risk of developing progressive multifocal leukoencephalopathy (PML) associated with administration of natalizumab to a patient comprising:
    before initiating or continuing natalizumab treatment, obtaining a specimen of cerebrospinal fluid (CSF) from the patient;
    testing the specimen for an indication of JC virus;
    withholding natalizumab treatment if JC virus is detected; or
    initiating or continuing with natalizumab treatment in the absence of an indication of JC virus.

2. The method of claim 1 in which natalizumab treatment is initiated or continues and further comprising the steps of:
    after a predetermined time, obtaining a subsequent specimen of cerebrospinal fluid from the patient;
    testing for the presence of an indication of JC virus in the subsequent specimen,
    interrupting the natalizumab treatment if JC virus is detected in the subsequent specimen; or
    continuing natalizumab treatment if JC virus is not detected.

3. The method of claim 2, further comprising repeating the steps at regular periodic intervals during the course of natalizumab treatment.

4. The method of claim 3, further comprising the step of repeating the method upon the appearance of a sign or symptom of PML.

5. The method of claim 4, wherein the method is repeated at least twice following the appearance of a sign or symptom of PML.

6. The method of claim 1, wherein the testing comprises Polymerase Chain Reaction (PCR).

7. The method of claim 1, wherein the patient had not previously received natalizumab treatment.

8. The method of claim 1, wherein the patient was previously receiving natalizumab treatment.

9. The method of claim 1, further comprising the step of preliminarily, and before the step of testing for indication of the JC virus, evaluating a magnetic resonance imaging (MRI) scan of the patient for evidence of PML.

10. The method of claim 9, further comprising the step of repeating the evaluation of a subsequent MRI scan of the patient before obtaining and screening a subsequent cerebrospinal fluid specimen for the presence of an indication of JC virus.

11. The method of claim 1, further comprising the steps of:
   screening the patient for PML by obtaining a magnetic resonance imaging (MRI) scan of the brain,
   determining the presence of PML by reference to the MRI image;
   withholding natalizumab treatment if the presence PML is detected in the MRI image; or
   continuing natalizumab treatment in the absence of an indication of PML in the MRI image and absence of an indication of JC virus in the CSF.

12. The method of claim 11 wherein the natalizumab treatment is continued and further comprising the steps of:
   after a predetermined time, obtaining a subsequent MRI scan image to screen for PML;
   determining the presence or absence of PML by reference to the subsequent MRI image;
   withholding natalizumab treatment if PML is detected from the subsequent MRI image; or
   continuing natalizumab treatment in the absence of an indication of PML in the subsequent MRI image and absence of an indication of JC virus in the CSF.

13. The method of claim 12 wherein the MRI scans of the patient are obtained and evaluated for an indication of PML at regular, periodic intervals during the course of natalizumab treatment.

14. The method of claim 11 wherein natalizumab treatment is continued, the method further comprising the steps of:
   obtaining and evaluating an MRI scan image of the patient at any time during the course of natalizumab treatment upon the appearance of signs or symptoms of PML;
   withholding natalizumab treatment if PML is detected from the MRI image; or
   continuing natalizumab treatment in the absence of an indication of PML in the MRI image and absence of an indication of JC virus in the CSF.

* * * * *